(12) United States Patent
Haverkost et al.

(10) Patent No.: US 11,109,867 B2
(45) Date of Patent: Sep. 7, 2021

(54) DEVICES AND METHODS FOR VEIN CLOSURE

(71) Applicant: BOSTON SCIENTIFIC SCIMED, INC., Maple Grove, MN (US)

(72) Inventors: Patrick A. Haverkost, Corcoran, MN (US); Arman Shahriar, Minneapolis, MN (US); Joel N. Groff, Delano, MN (US); John LaRoy, Minneapolis, MN (US); John Mundahl, Minnetonka, MN (US); Eric Cooper, Minneapolis, MN (US)

(73) Assignee: BOSTON SCIENTIFIC SCIMED, INC., Maple Grave, MN (US)

( * ) Notice: Subject to any disclaimer, the term of this patent is extended or adjusted under 35 U.S.C. 154(b) by 262 days.

(21) Appl. No.: 16/355,699

(22) Filed: Mar. 15, 2019

(65) Prior Publication Data
US 2019/0282241 A1    Sep. 19, 2019

Related U.S. Application Data

(60) Provisional application No. 62/643,832, filed on Mar. 16, 2018.

(51) Int. Cl.
| A61B 17/12 | (2006.01) |
| A61B 17/00 | (2006.01) |
| A61B 90/00 | (2016.01) |

(52) U.S. Cl.
CPC .... *A61B 17/12109* (2013.01); *A61B 17/1204* (2013.01); *A61B 17/12031* (2013.01);
(Continued)

(58) Field of Classification Search
CPC ........ A61B 17/12109; A61B 17/12172; A61B 17/12031; A61B 17/12168;
(Continued)

(56) References Cited

U.S. PATENT DOCUMENTS 3,687,129 A * 8/1972 Nuwayser ................ A61F 6/22
128/843
3,834,394 A   9/1974 Hunter et al.
(Continued)

FOREIGN PATENT DOCUMENTS

AU    2008229892 A1    10/2008
EP       1686903 B1     7/2014
(Continued)

OTHER PUBLICATIONS

International Search Report and Written Opinion dated Jun. 25, 2019 for International Application No. PCT/US2019/022642.

*Primary Examiner* — Julian W Woo
(74) *Attorney, Agent, or Firm* — Seager, Tufte & Wickhem, LLP

(57) ABSTRACT

An implant for occluding a flow through a vessel may comprise a body member having a first end portion, a second end portion, and an intermediate rod portion extending between the first end portion and the second end portion and a mesh having base layer and a plurality of micro-pillars extending from a first surface of the base layer. The mesh may be disposed about at least a portion of the body such that the micro-pillars extending generally radially outward from the body member. The plurality of micro-pillars may be configured to extend into an adjacent tissue.

19 Claims, 17 Drawing Sheets

(52) U.S. Cl.
CPC .. *A61B 17/12168* (2013.01); *A61B 17/12172* (2013.01); *A61B 17/0057* (2013.01); *A61B 17/1214* (2013.01); *A61B 2017/00004* (2013.01); *A61B 2017/1205* (2013.01); *A61B 2017/12054* (2013.01); *A61B 2090/3954* (2016.02); *A61B 2090/3966* (2016.02)

(58) Field of Classification Search
CPC ...... A61B 17/1204; A61B 2017/00004; A61B 2017/12054; A61B 17/0057; A61B 17/1214; A61B 2017/1205
See application file for complete search history.

(56) References Cited

U.S. PATENT DOCUMENTS

| | | | |
|---|---|---|---|
| 4,085,757 A | 4/1978 | Pevsner | |
| 4,213,461 A | 7/1980 | Pevsner | |
| RE32,348 E | 2/1987 | Pevsner | |
| 4,705,517 A | 11/1987 | DiPisa, Jr. | |
| 4,994,069 A | 2/1991 | Richart et al. | |
| 5,167,614 A | 12/1992 | Tessmann et al. | |
| 5,382,259 A * | 1/1995 | Phelps | A61B 17/1215 606/151 |
| 5,382,261 A | 1/1995 | Palmaz | |
| 5,417,708 A * | 5/1995 | Hall | A61B 17/12022 606/200 |
| 5,456,693 A | 10/1995 | Conston et al. | |
| 5,656,036 A | 8/1997 | Palmaz | |
| 5,667,767 A | 9/1997 | Greff et al. | |
| 5,676,962 A | 10/1997 | Garrido et al. | |
| 5,702,421 A * | 12/1997 | Schneidt | A61B 17/0057 600/32 |
| 5,733,294 A | 3/1998 | Forber et al. | |
| 5,830,178 A | 11/1998 | Jones et al. | |
| 5,851,508 A | 12/1998 | Greff et al. | |
| 6,572,873 B1 | 6/2003 | Osman et al. | |
| 6,638,293 B1 | 10/2003 | Makower et al. | |
| 6,726,674 B2 | 4/2004 | Leu | |
| 6,941,169 B2 * | 9/2005 | Pappu | A61N 1/3621 607/9 |
| 7,007,698 B2 | 3/2006 | Thornton | |
| 7,077,836 B2 | 7/2006 | Lary et al. | |
| 7,201,758 B2 | 4/2007 | Farmache | |
| 7,303,571 B2 | 12/2007 | Makower et al. | |
| 7,314,466 B2 | 1/2008 | Lary et al. | |
| 7,331,199 B2 | 2/2008 | Ory et al. | |
| 7,402,320 B2 | 7/2008 | Mirizzi et al. | |
| 7,682,385 B2 | 3/2010 | Thornton | |
| 7,998,188 B2 | 8/2011 | Zilla et al. | |
| 8,029,560 B2 | 10/2011 | Bates et al. | |
| 8,057,537 B2 | 11/2011 | Zilla et al. | |
| 8,172,746 B2 | 5/2012 | Zilla et al. | |
| 8,313,533 B2 | 11/2012 | Goldmann | |
| 8,382,814 B2 | 2/2013 | Zilla et al. | |
| 8,469,994 B2 | 6/2013 | LaFontaine | |
| 8,475,492 B2 | 7/2013 | Raabe et al. | |
| 8,518,104 B2 | 8/2013 | Bates et al. | |
| 8,747,451 B2 | 6/2014 | Zilla et al. | |
| 8,845,614 B2 | 9/2014 | Raabe et al. | |
| 8,906,082 B2 | 12/2014 | Zilla et al. | |
| 9,011,486 B2 | 4/2015 | Raabe et al. | |
| 9,017,361 B2 | 4/2015 | Karabey et al. | |
| 9,414,843 B2 | 8/2016 | Pavcnik et al. | |
| 9,474,514 B2 * | 10/2016 | Agnew | A61B 17/0057 |
| 9,517,069 B2 | 12/2016 | Zilla et al. | |
| 9,517,121 B2 | 12/2016 | Zilla et al. | |
| 9,561,023 B2 | 2/2017 | Raabe et al. | |
| 9,592,037 B2 | 3/2017 | Raabe et al. | |
| 9,844,653 B2 * | 12/2017 | Conder | A61B 17/12172 |
| 10,299,797 B2 * | 5/2019 | Bradway | A61B 17/12031 |
| 10,470,773 B2 * | 11/2019 | Maguire | A61B 17/12109 |
| 10,660,645 B2 * | 5/2020 | Allen | A61B 17/12163 |
| 2003/0206864 A1 | 11/2003 | Mangin | |
| 2004/0098030 A1 | 5/2004 | Makower et al. | |
| 2005/0004598 A1 * | 1/2005 | White, Jr. | A61B 17/1215 606/200 |
| 2005/0107867 A1 | 5/2005 | Taheri | |
| 2005/0149173 A1 * | 7/2005 | Hunter | A61B 17/11 623/1.42 |
| 2005/0174384 A1 | 12/2005 | Tran et al. | |
| 2006/0052822 A1 | 3/2006 | Mirizzi et al. | |
| 2006/0052823 A1 | 3/2006 | Mirizzi et al. | |
| 2006/0135947 A1 | 6/2006 | Soltesz et al. | |
| 2006/0190076 A1 | 8/2006 | Taheri | |
| 2006/0282158 A1 | 12/2006 | Taheri | |
| 2006/0282159 A1 | 12/2006 | Taheri | |
| 2007/0166345 A1 | 7/2007 | Pavcnik et al. | |
| 2007/0208417 A1 | 9/2007 | Agnew | |
| 2007/0292472 A1 | 12/2007 | Paul et al. | |
| 2007/0293932 A1 | 12/2007 | Zilla et al. | |
| 2008/0045996 A1 | 2/2008 | Makower et al. | |
| 2009/0069758 A1 | 3/2009 | Bates et al. | |
| 2010/0217306 A1 | 8/2010 | Raabe et al. | |
| 2010/0217313 A1 | 8/2010 | Raabe et al. | |
| 2011/0060277 A1 | 3/2011 | Lilley | |
| 2011/0295157 A1 | 12/2011 | Zilla et al. | |
| 2011/0295233 A1 | 12/2011 | Bates et al. | |
| 2012/0109191 A1 | 5/2012 | Marano, Jr. et al. | |
| 2013/0072907 A1 | 3/2013 | Lichty, II et al. | |
| 2013/0144374 A1 | 6/2013 | Zilla et al. | |
| 2014/0039352 A1 | 2/2014 | Zilla et al. | |
| 2014/0379010 A1 | 12/2014 | Zilla et al. | |
| 2015/0005804 A1 | 1/2015 | Franano et al. | |
| 2015/0018857 A1 | 1/2015 | Elgaard et al. | |
| 2015/0265264 A1 | 9/2015 | Raabe et al. | |
| 2015/0313602 A1 | 11/2015 | Rudakov | |
| 2015/0343181 A1 | 12/2015 | Bradway et al. | |
| 2016/0346423 A1 | 12/2016 | Morales | |
| 2017/0143349 A1 | 5/2017 | Raabe et al. | |

FOREIGN PATENT DOCUMENTS

| | | |
|---|---|---|
| EP | 2398402 B1 | 4/2016 |
| EP | 3028650 A1 | 6/2016 |
| JP | 2003275218 A | 9/2003 |
| WO | 2005048884 A1 | 6/2005 |
| WO | 20050535547 A2 | 6/2005 |
| WO | 2005074845 A1 | 8/2005 |
| WO | 2007016122 A2 | 2/2007 |
| WO | 2008137646 A1 | 11/2008 |
| WO | 2009036250 A1 | 3/2009 |
| WO | 2010022072 A1 | 2/2010 |
| WO | 2010096717 A1 | 8/2010 |
| WO | 2015105878 A1 | 7/2015 |
| WO | 2017161283 A1 | 9/2017 |

* cited by examiner

DEVICES AND METHODS FOR VEIN CLOSURE

CROSS-REFERENCE TO RELATED APPLICATIONS

This application claims the benefit of priority under 35 U.S.C. § 119 of U.S. Provisional Application No. 62/643,832, filed Mar. 16, 2018, the entire disclosure of which is hereby incorporated by reference.

TECHNICAL FIELD

The present disclosure pertains to medical devices and methods for manufacturing and/or using medical devices. More particularly, the present disclosure pertains to configurations of a system for closing body lumens.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

The disclosure is directed to several alternative designs, materials and methods of manufacturing medical device structures and assemblies.

In a first example, an implant for occluding a flow through a vessel may comprise a body member having a first end portion, a second end portion, and an intermediate rod portion extending between the first end portion and the second end portion and a mesh having a base layer and a plurality of micro-pillars extending from a first surface of the base layer, the mesh disposed about at least a portion of the body such that the micro-pillars extending generally radially outward from the body member. The plurality of micro-pillars may be configured to extend into an adjacent tissue.

Alternatively or additionally to any of the examples above, in another example, the mesh may be disposed about the intermediate rod portion.

Alternatively or additionally to any of the examples above, in another example, the intermediate rod portion may be configured to bend.

Alternatively or additionally to any of the examples above, in another example, the first end portion and the second portion may have a generally spherical shape.

Alternatively or additionally to any of the examples above, in another example, the implant may have a generally uniform outer diameter.

Alternatively or additionally to any of the examples above, in another example, the base layer may be a knitted fabric formed from a single strand.

Alternatively or additionally to any of the examples above, in another example, the base layer may be a knitted fabric formed from one or more strands.

Alternatively or additionally to any of the examples above, in another example, the base layer may be a knitted fabric formed from two or more strands.

Alternatively or additionally to any of the examples above, in another example, the micro-pillars may be knitted into the base layer.

Alternatively or additionally to any of the examples above, in another example, the base layer may be a woven fabric formed from one or more strands.

Alternatively or additionally to any of the examples above, in another example, the micro-pillars may be woven into the base layer.

Alternatively or additionally to any of the examples above, in another example, the mesh may be disposed over at least a portion of one or both the first or second end portions.

Alternatively or additionally to any of the examples above, in another example, the mesh may be disposed over the intermediate rod portion and at least a portion of one or both the first or second end portions.

Alternatively or additionally to any of the examples above, in another example, the mesh may comprise a bioabsorable material.

Alternatively or additionally to any of the examples above, in another example, at least some of the plurality of micro-pillars may extend at a generally orthogonal angle to the base layer.

Alternatively or additionally to any of the examples above, in another example, at least some of the plurality of micro-pillars may extend at a generally non-orthogonal angle to the base layer.

Alternatively or additionally to any of the examples above, in another example, the body member may comprise a bioabsorable material.

In another example, a method for delivering an implant to a body vessel may comprise advancing a guide catheter and an implant within a body vessel. The implant may comprise a body member having a first end portion, a second end portion, and an intermediate rod portion extending between the first end portion and the second end portion and a mesh having base layer and a plurality of micro-pillars extending from a first surface of the base layer, the mesh disposed about at least a portion of the body such that the micro-pillars extending generally radially outward from the body member. A distal end region of the guide catheter may be positioned adjacent to a target region within the body vessel and a distal opening of the guide catheter may be directed towards a side wall of the body vessel. The implant may be distally advanced through the distal opening of the guide catheter towards the side wall of the body vessel. As the implant is distally advanced through the distal opening of the guide catheter, the plurality of micro-pillars along a portion of the mesh may be pushed into the side wall of the vessel.

Alternatively or additionally to any of the examples above, in another example, the method may further comprise compressing an inner surface of the vessel about an outer surface of the implant.

Alternatively or additionally to any of the examples above, in another example, compressing the inner surface of the vessel about an outer surface of the implant may comprise exerting a physical force on a surface of a patient's body above the target location.

Alternatively or additionally to any of the examples above, in another example, the physical force may be a pneumatic cuff.

Alternatively or additionally to any of the examples above, in another example, compressing the inner surface of the vessel about an outer surface of the implant may comprise delivering a negative pulse wave to the vessel adjacent to the target region.

Alternatively or additionally to any of the examples above, in another example, delivering the negative pulse wave may comprise advancing a stimulation catheter having an electrode through the body vessel to the target region.

Alternatively or additionally to any of the examples above, in another example, compressing the inner surface of the vessel about an outer surface of the implant may comprise delivering a vasospasm inducing target to the target region.

Alternatively or additionally to any of the examples above, in another example, the vasospasm inducing drug may be coated on an outer surface of the implant.

In another example, an implant and delivery system kit may comprise one or more implants and a delivery system. The one or more implants may comprise a body member having a first end portion, a second end portion, and an intermediate rod portion extending between the first end portion and the second end portion and a mesh having base layer and a plurality of micro-pillars extending from a first surface of the base layer, the mesh disposed about at least a portion of the body such that the micro-pillars extending generally radially outward from the body member. The delivery system may comprise a guide catheter defining a lumen extending from a proximal end region to a distal opening and a pusher element having an elongate shaft and pusher head positioned at a distal end of the elongate shaft;

Alternatively or additionally to any of the examples above, in another example, the one or more implants may be pre-loaded within the lumen of the guide catheter. In another example, a self-fixating mesh may comprise a base layer having a top surface and a bottom surface and a plurality of micro-pillars extending from the top surface of the base layer. The plurality of micro-pillars may be configured to extend into a body tissue.

Alternatively or additionally to any of the examples above, in another example, the base layer may be a knitted fabric formed from a single strand.

Alternatively or additionally to any of the examples above, in another example, the base layer may be a knitted fabric formed from two or more strands.

Alternatively or additionally to any of the examples above, in another example, the strand may be a monofilament strand.

Alternatively or additionally to any of the examples above, in another example, the strand may be a multifilament strand.

Alternatively or additionally to any of the examples above, in another example, the micro-pillars may be knitted into the base layer.

Alternatively or additionally to any of the examples above, in another example, the base layer may be a woven fabric formed from one or more strands.

Alternatively or additionally to any of the examples above, in another example, the micro-pillars may be woven into the base layer.

Alternatively or additionally to any of the examples above, in another example, the strand may be a monofilament strand.

Alternatively or additionally to any of the examples above, in another example, the strand may be a multifilament strand.

Alternatively or additionally to any of the examples above, in another example, at least some of the plurality of micro-pillars may extend at a generally orthogonal angle to the base layer.

Alternatively or additionally to any of the examples above, in another example, at least some of the plurality of micro-pillars may extend at a generally non-orthogonal angle to the base layer.

Alternatively or additionally to any of the examples above, in another example, the mesh may comprise a bioabsorable material.

Alternatively or additionally to any of the examples above, in another example, the mesh may comprise two or more different materials.

In another example, a method for manufacturing a self-fixating mesh may comprise warping one or more strands onto one or more warp beams, loading the one or more warp beams into a knitting machine, knitting a spacer fabric having a top fabric layer, a bottom fabric layer, and a plurality of spacer filaments extending between the top fabric layer and the bottom fabric layer, and cutting the spacer fabric through the plurality of spacer filaments to form a first self-fixating mesh and a second self-fixating mesh. The first self-fixating mesh may comprise the top fabric layer and a first portion of a length of the plurality of spacer filaments and the second self-fixating mesh may comprise the bottom fabric layer and a second portion of a length of the plurality of spacer filaments.

In another example, a method for manufacturing a self-fixating mesh may comprise warping one or more strands onto one or more warp beams, loading the one or more warp beams into a weaving loom, weaving a spacer fabric having a top fabric layer, a bottom fabric layer, and a plurality of spacer filaments extending between the top fabric layer and the bottom fabric layer, and cutting the spacer fabric through the plurality of spacer filaments to form a first self-fixating mesh and a second self-fixating mesh. The first self-fixating mesh may comprise the top fabric layer and a first portion of a length of the plurality of spacer filaments and the second self-fixating mesh may comprise the bottom fabric layer and a second portion of a length of the plurality of spacer filaments. Alternatively or additionally to any of the examples above, in another example, the top fabric layer may have a first configuration and the bottom fabric layer may have a second configuration different from the first configuration.

Alternatively or additionally to any of the examples above, in another example, the one or more strands may comprise a monofilament strand.

Alternatively or additionally to any of the examples above, in another example, the one or more stands may comprise a multifilament strand.

Alternatively or additionally to any of the examples above, in another example, the one or more strands may comprise a bioabsorbable material.

Alternatively or additionally to any of the examples above, in another example, the plurality of spacer filaments may comprise a material different from a bulk of the top or bottom fabric layers.

Alternatively or additionally to any of the examples above, in another example, the method may further comprise annealing the first and second self-fixating meshes.

Alternatively or additionally to any of the examples above, in another example, at least some of the plurality of spacer filaments may extend at a generally orthogonal angle to the top and/or bottom fabric layers.

Alternatively or additionally to any of the examples above, in another example, at least some of the plurality of spacer filaments may extend at a generally non-orthogonal angle to the top and/or bottom fabric layers.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1A:
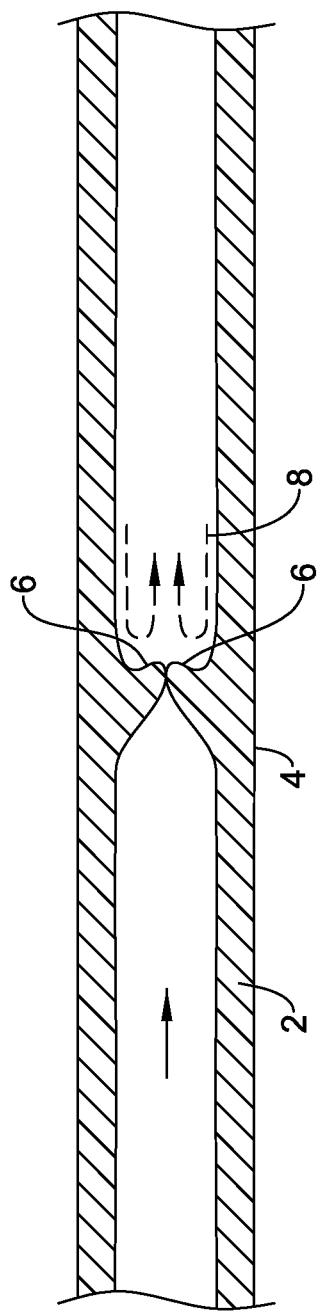
FIG. 1A is cross-sectional view of an illustrative vessel having a healthy venous valve.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Healthy leg veins contain valves that allow blood to move in one direction from the lower limbs toward the heart. Referring to FIG. 1A, a healthy venous valve 4 is illustrated in a vessel 2. The valve 4 is bicuspid, with opposed cusps 6. In the closed condition, the cusps 6 are drawn together to prevent retrograde flow (arrow 8) of blood. These valves 4 open when blood is flowing toward the heart, and close to prevent venous reflux (also known as venous insufficiency), or the backward flow of blood. When veins weaken and become enlarged, their valves cannot close properly, which leads to venous reflux and impaired drainage of venous blood from the legs. Incompetence of a venous valve is thought to arise from at least the following two medical conditions varicose veins and chronic venous insufficiency. In some cases, pelvic congestion can result in or contribute to varicose veins.

Figure 1B:
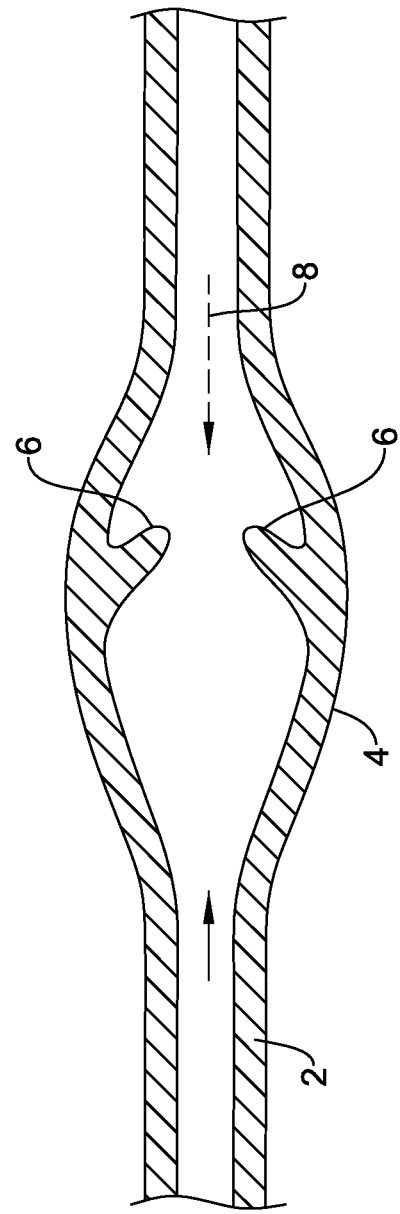
FIG. 1B is a cross-section view of an illustrative vessel having an incompetent venous valve.

Referring to FIG. 1B, if the valve 4 is incompetent, the cusps 6 do not seal properly and retrograde flow of blood occurs. Venous reflux is most common in the superficial veins. The largest superficial vein is the great saphenous vein, which runs from the top of the foot to the groin, where it originates at a deep vein. Factors that contribute to venous reflux disease include female gender, heredity, obesity, lack of physical activity, multiple pregnancies, age, past history of blood clots in the legs and professions that involve long periods of standing. According to population studies, the prevalence of visible tortuous varicose veins, a common indicator of venous reflux disease, is up to 15% for adult men and 25% for adult women. Venous reflux can be classified as either asymptomatic or symptomatic, depending on the degree of severity. Symptomatic venous reflux disease is a more advanced stage of the disease and can have a profound impact on the patient's quality of life. People with symptomatic venous reflux disease may seek treatment due to a combination of symptoms and signs, which may include leg pain and swelling, painful varicose veins; skin changes such as discoloration or inflammation, and/or open skin ulcers. A primary goal of treating symptomatic venous reflux is to eliminate the reflux at its source. Such as, for example, the great saphenous vein. If a diseased vein is either closed or removed, blood can automatically reroute into other veins without any known negative consequences to the patient.

There are several treatments available for superficial vein insufficiency and/or pelvic congestion syndrome including, but not necessarily limited to, the use of adhesives delivered endovenously, thermal ablation (radiofrequency, laser, microwave, or steam), mechanochemical ablation (MOCA), foam sclerotherapy, hormone therapy, coils, ligation and stripping, ambulatory phlebectomy, and/or venoactive drugs. However, these treatments may include some drawbacks. For example, ablation may be painful to the patient. Foams and other treatments designed to desiccate or occlude the vessel may enter small branches off the vessel where treatment is not desired. Adhesive systems may lack the holding power required to maintain the vessel in a closed configuration. Further, superficial vein insufficiency and pelvic congestion syndrome may require different treatments due to varying locations within the body. What may be desirable is alternative treatment systems and methods that may treat both pelvic congestion syndrome and superficial vein insufficiency.

Figure 2:
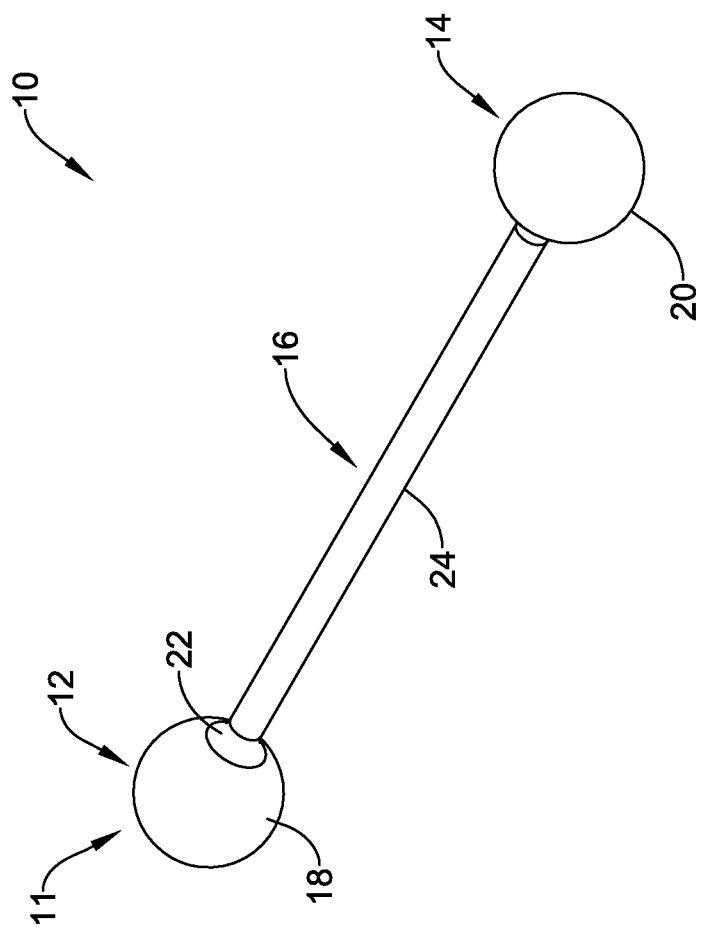
FIG. 2 is a perspective view of an illustrative implant.

FIG. 2 is a perspective view of an illustrative implant 10 for occluding a vessel or lumen such, as but not limited to, a blood vessel. The implant 10 may have a body portion or member 11 extending from a first end region 12 to a second end region 14. The end regions 12, 14 may be interconnected by an intermediate region 16. In some instances, the intermediate region 16 may have a smaller diameter or cross-sectional area relative to the first end 12 and/or second end 14. However, this is not necessarily required. The first end region 12 may include a generally spherical first end portion 18. The second end region 14 may also include a generally spherical second end portion 20. While the end portions 18, 20 are described as generally spherical, it is contemplated that the end portions 18, 20 may take any shape desired, such as but not limited to, hemispherical, ellipsoid, cubic, conical, or any three-dimensional shape desired.

In some instances, the implant 10 may be sized to fit within an 8 French guide catheter. For example, the first and second end portions 18, 20 may have an outer dimension in the range of about 2.5 to about 2.6 millimeters (mm). However, it is contemplated that the implant 10 may be of various sized to accommodate a range of vessel diameters. For example, the end portions 18, 20 of implant 10 may be in the range of 1 to 20 mm or in the range of about 1 to about 10 mm, etc. However, these are just an example. It is contemplated that the size of the implant 10 (and/or various components thereof) may be selected to best suit the size of the vessel it is to be positioned within and an appropriately sized guide catheter may be utilized for the delivery of the implant 10. For example, if so desired, the implant 10 may be sized for delivery within the cutaneous venous system, the superficial venous system, and/or the deep venous system as desired. Further, it is contemplated that a length of the implant 10 may be varied depending on the vessel it is to be implanted. For example, a length of the implant 10 may range from about 0.5 centimeters (cm) to about 5 cm. Shorter implants 10 may be used in tortuous vessels which may require many implants to be positioned within the curving vessel. In some cases, shorter implants 10 may also allow for more precision in the beginning and/or end location of the implant(s) 10. Further, when two or more implants 10 are to be implanted in series (as will be described herein), shorter implants may allow for more flexibility (e.g., providing more bend points between adjacent implants 10) while longer implants 10 may reduce flexibility. Longer implants 10 may be used in continuous vessel lengths.

Further, while the first end portion 18 and second end portion 20 are shown as having generally the same or similar shape, it is contemplated that the first end portion 18 and second end portion 20 may take differing shapes, as desired. For example, the first end portion 18 and second end portion 20 may be formed from mating shapes configured to allow for connection of adjacent implants 10 within a vessel. In some instances, the end portions 18, 20 may include a twist to lock feature where one of the end portions 18, 20 includes a protruding shape configured to engage a mating recess in the other of the end portions 18, 20 of an adjacent implant 10. Once a protruding shape is engaged within the mating recess, rotation of the implant 10, including the protruding shape, locks the protruding shape within the recess of the second implant 10. This is just one example. It is contemplated that the end portions 18, 20 may include other features configured to facilitate connection of two or more implants 10 configured to be positioned within the same vessel. In some cases, one or both the end portions 18, 20 may be configured to have a split end, such as a "Y" configuration, to couple to an adjacent implant 10 in a branching or tributary vessel.

The end portions 18, 20 may be interconnected by a rod portion 24. As described above, the rod portion 24 may have a smaller cross-sectional area than the end portions 18, 20. The rod portion 24 may be configured to be flexible or bendable to facilitate delivery of the implant 10, it will be described in more detail herein. It is contemplated that the body 11 of the implant 10 may be formed from any biocompatible material desired such as, but not limited to, Teflon®, titanium, metal, polymers, composites, etc. In some instances, the implant 10 may be formed from a bioabsorbable material. This may allow an implant 10 to be temporarily positioned within a vessel for a predetermined length of time (e.g., 1 year or less, 1 month or less, 1 week or less, 1 day or less, etc.) giving the physician and/or the patient a chance to evaluate if the treatment is beneficial prior to permanent closure of the vessel. However, the implant 10 need not be bioabsorbable to accomplish a trial treatment. For example, the implant 10 may be mechanically deconstructed or chemically deconstructed. It is further contemplated that the material should be selected and/or sized such that at least the intermediate rod portion 24 is bendable. In some instances, the end portions 18, 20 may be coupled to the intermediate rod portion 24 by a tapered interconnecting waist 22. The body 11 of the implant 10 may be formed as a single unitary structure using techniques such as, but not limited to, molding, laser cutting, drawing, casting, etc. In other instances, one or more of the components (e.g., first end portion 18, a second end portion 20, and/or intermediate rod 24) of the implant 10 may be formed as individual pieces which are subsequently connected using techniques such as, but not limited, to adhesives, heat bonding, mechanical connections (e.g., snap-fit, screws, etc.), welding, brazing, etc.

Figure 3:
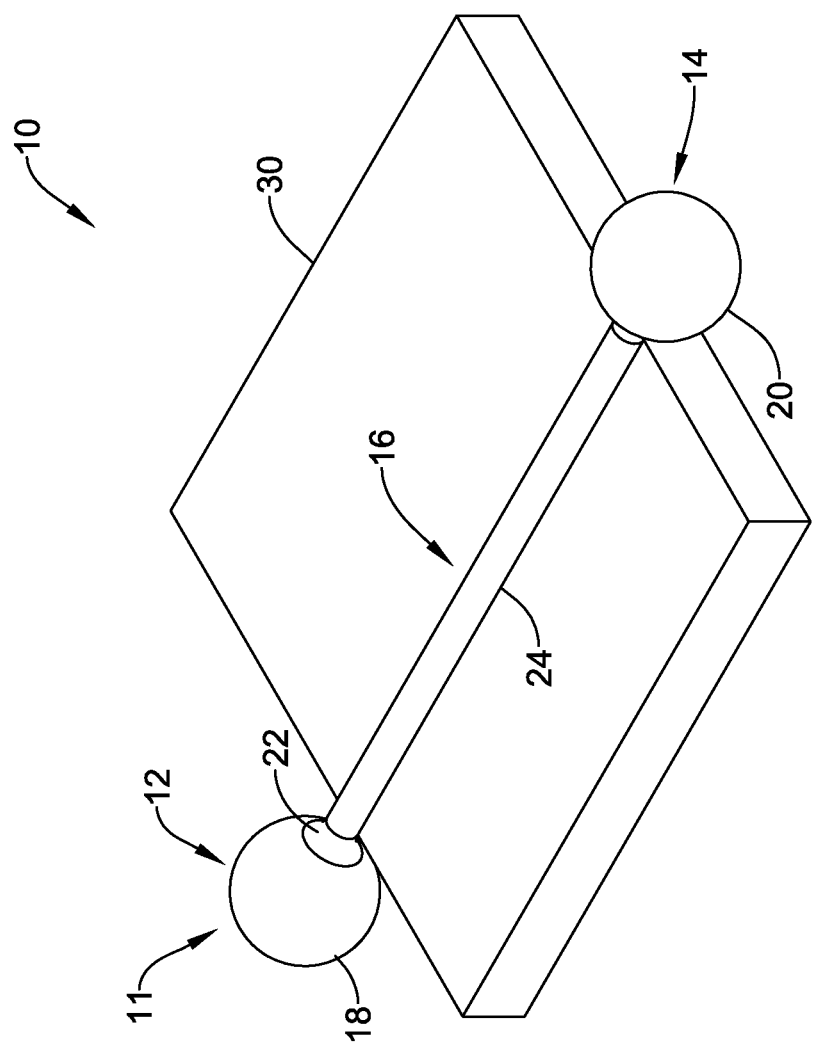
FIG. 3 is a perspective view of the illustrative implant of FIG. 2 having a self-fixating mesh assembled therewith.
Figure 4:
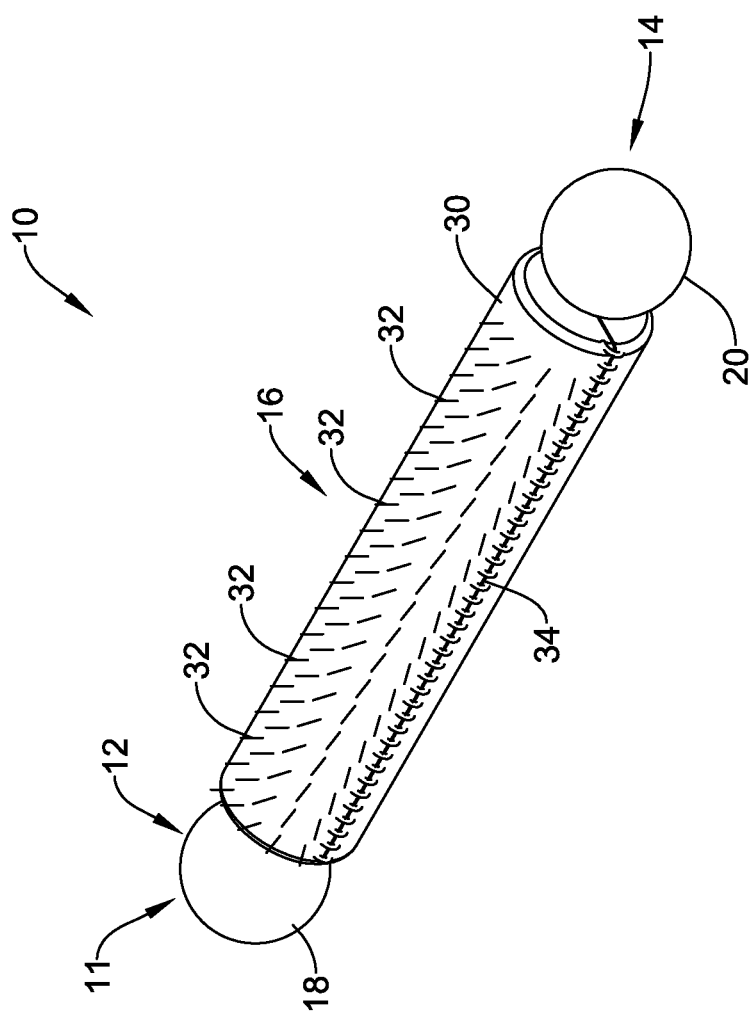
FIG. 4 is a perspective view of the illustrative implant of FIG. 2 including a self-fixating mesh.

In some embodiments, the implant 10 may be further provided with a mesh or fabric positioned about the intermediate rod 24. FIG. 3 illustrates a perspective view of the illustrative implant 10 with the rod 24 resting on a length of mesh 30. The mesh 30 may be a woven or knitted fabric having a plurality of micro-pillars extending from a surface thereof. The micro-pillars may be configured to extend into a vessel wall or adjacent tissue such that the implant 10 may be self-adhering or self-fixating, as will be described in more detail herein. The mesh 30 may be wrapped around the intermediate rod portion 24, as shown in FIG. 4. The mesh 30 may be tacked or secured about the intermediate rod portion 24 using, for example, sutures 34, adhesives, or other securement means.

The mesh 30 may be positioned about the intermediate rod portion 24 such that a plurality of micro-pillars 32 extend radially outward (e.g., away from the rod portion 24).

When positioned within a vessel, the micro-pillars 32 may be configured to extend into the vessel wall to fixate the implant 10 within the vessel, as will be described in more detail herein. It is contemplated that the mesh 30 may have a thickness such that when the mesh 30 is disposed about the intermediate rod 24, the implant 10 has a substantially uniform outer diameter (or cross-section for a non-circular cross-section) from the first end region 12 to the second end region 14. However, this is not required. For example, the thickness of the mesh 30 may be selected such that intermediate region 16 (and/or the region having the mesh 30 disposed thereabout) has a smaller cross-sectional dimension or a larger cross-sectional than one or both of the end portions 18, 20, as a desired. In some embodiments, the mesh 30 may have a thickness in the range of about 0.5 mm to about 5 mm. It is further contemplated that the mesh 30 may extend over an entire length of the intermediate rod portion 24 or less than an entire length thereof, as desired. For example, while the self-fixating mesh 30 is illustrated as disposed about the intermediate rod portion 24, the mesh 30 may cover or partially cover one or both of the first or second end portions 18, 20, as desired. Disposing the mesh 30 over one or both end portions 18, 20 may ensure a stronger fixation between the implant 10 and the vessel, although this is not required.

Figure 5:
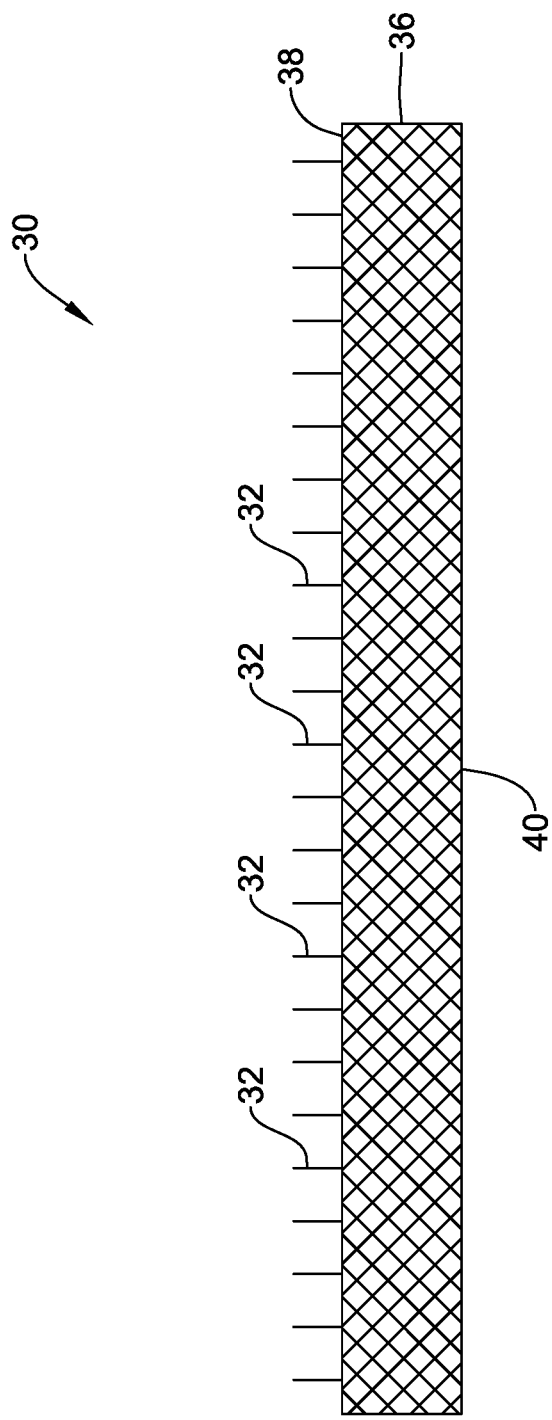
FIG. 5 is a cross-sectional view of an illustrative self-fixating mesh.

FIG. 5 is a cross-sectional view of an illustrative self-fixating mesh 30 for use with the implant 10. The mesh 30 may include a fabric base layer or substrate 36 with a plurality of micro-pillars 32 extending from a top surface 38 thereof. The thickness of the base layer 36 may be dependent on the yarn or filament used to form the mesh 30. In some cases, the base layer 36 may have a thickness in the range of about 0.5 mm to about 5 mm. The micro-pillars 32 may have a length in the range of about 0.25 mm to about 1 mm. The base layer 36 may further include a back surface 40. The back surface 40 may be configured to contact the rod portion 24. While the micro-pillars 32 are illustrated as extending generally orthogonally from the base layer 36, it is contemplated that the micro-pillars 32 may extend at any angle between 0° and 180° relative to the top surface 38 of the base layer 36. It is further contemplated that the micro-pillars 32 may be arranged in patterns (e.g., rows, clusters, etc.) or eccentrically, as desired. Further, the micro-pillars 32 need not all extend at the same angle. For example, some micro-pillars 32 may extend generally orthogonally, some may extend at an angle less than 90° and some may extend at an angle greater than 90°. The self-fixating mesh 30 may be formed by initially producing a spacer fabric and subsequently cleaving the spacer fabric to generate two pieces of self-fixating mesh 30.

Figure 6:
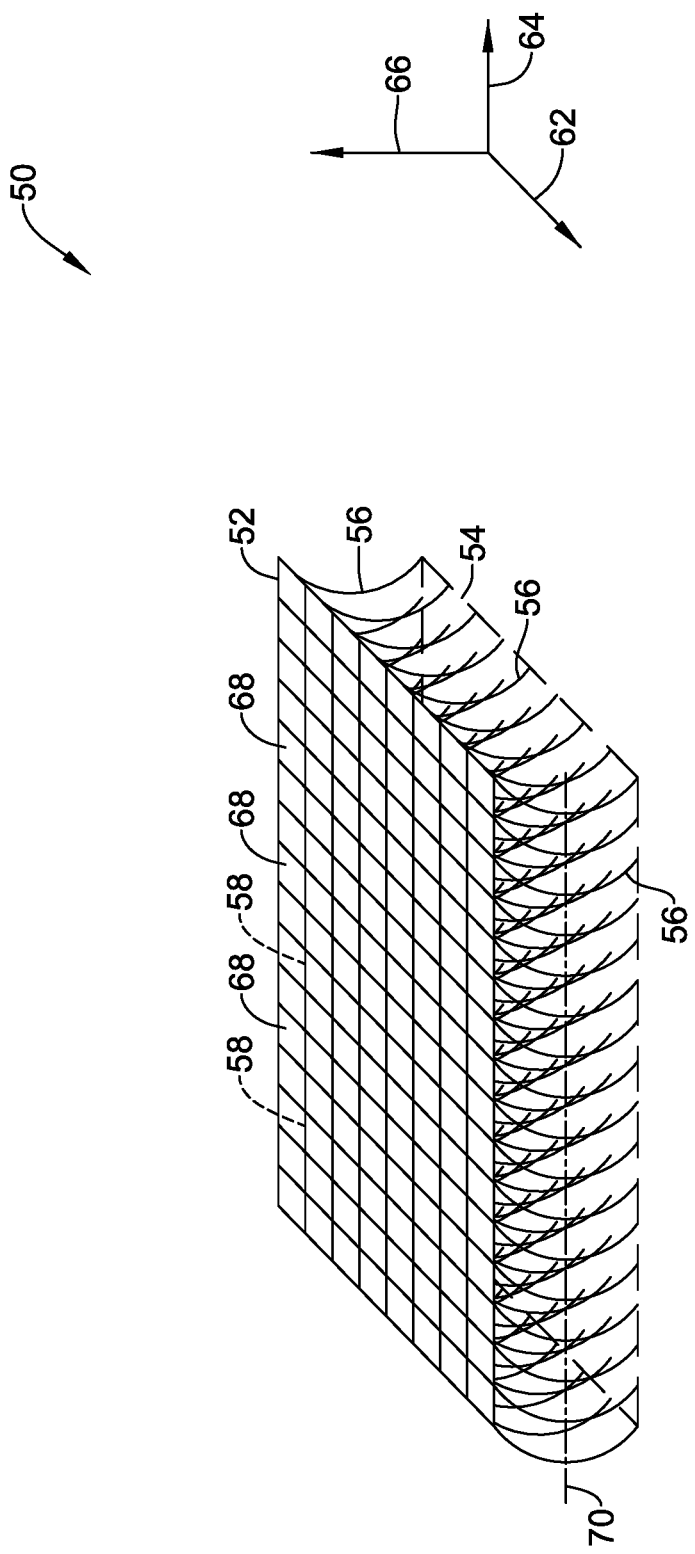
FIG. 6 is a perspective view of an illustrative spacer fabric for forming a self-fixating mesh.

FIG. 6 is a schematic perspective view of an illustrative spacer fabric 50 utilized to produce the self-fixating mesh 30. The spacer fabric 50 may include a top fabric layer 52, a bottom fabric layer 54, and a plurality of spacer filaments 56 extending between and the top fabric layer 52 and the bottom fabric layer 54. The top layer 52, the bottom layer 54 and a plurality of spacer filaments 56 may be formed at the same time. For example, the spacer fabric 50 may be knitted from one or more yarn elements 58 using a knitting or weaving machine. The yarn element or strand 58 may be split and warped onto one or more warp beams which are then fed or loaded into a knitting machine or weaving loom to produce the spacer fabric configuration having the top fabric layer 52, bottom fabric layer 54, and spacer filaments 56.

In some cases, the spacer fabric 50 may be formed from a single monofilament yarn, a single multi-filament yarn, two or more monofilament yarns, two or more multifilament yarns, or a combination of one or more monofilament and one or more multifilament yarns, as desired. The type (e.g., mono- or multi-filament and/or material) and number of yarn strands 58 used to form the illustrative spacer fabric 50 may be selected to vary the properties of the top layer 52, bottom layer 54, and/or spacer filaments 56.

It is further contemplated the material of the yarn 58 may be selected to achieve desired properties. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. In some instances, the yarn may be formed from a bioabsorbable polymer such as, but not limited to, polylactic acid (PLA), polypropylene (PPL), poly(glycolic acid) (PGA), nylon, or poly(trimethylene terephthalate) (PTT). Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some instances, it may be desirable for both the body 11 of the implant 10 and the self-fixating mesh 30 to be bioabsorbable. This may limit negative bioreactivity to foreign body implants and increase the flexibility of the vessel once closed. It is contemplated that only one of the body 11 or the mesh 30 being bioabsorbable may similarly limit negative bioreactivity to foreign body implants and increase the flexibility of the vessel once closed.

It is contemplated that the top layer 52 and/or the bottom layer 54 may be woven or knitted, as desired. For example, the top layer 52 and/or the bottom layer 54 may include one or more strands 58 extending in a weft direction 62 and one or more strands 58 extending in a warp direction 64. In some instances, the top layer 52 and/or the bottom layer 54 may be formed from a single strand or a plurality of strands, as desired. In some cases, different strands of different materials may be interwoven or knitted together to achieve a desired property in the top layer 52, bottom layer 54, and/or spacer filaments 56.

The top layer 52 and/or the bottom layer 54 may be formed using any knitting or weaving technique desired. It is further contemplated that the top layer 52 and the bottom layer 54 need not both have the same woven or knitted pattern. For example, while formed at the same time, the design of each of the top layer 52 and the bottom layer 54 may be tailored individually. It is further contemplated that the knitting or weaving pattern of the top layer 52 may be varied in the weft direction 62 or the warp direction 64. For example, the top layer 52 may have regions of open knit or open weave and regions of tight knit or tight weave. Similarly, if so desired, the bottom layer 54 may also include different weaving or knitting patterns.

Figure 7B:
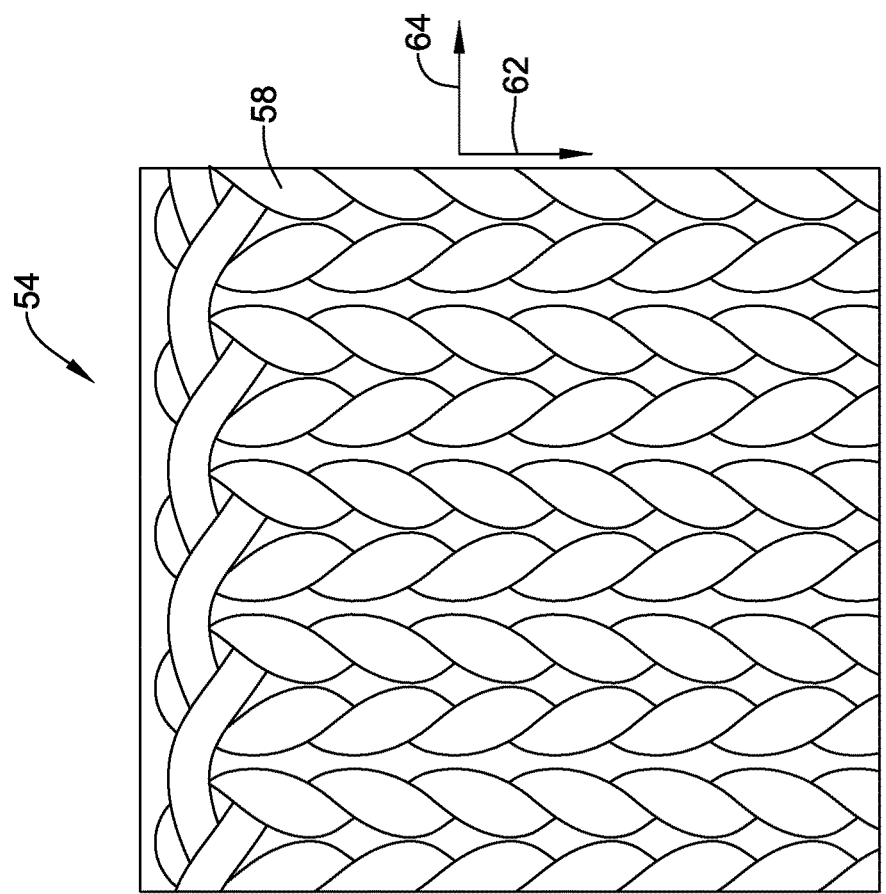
FIG. 7B is a bottom view of another illustrative layer of a spacer fabric.
Figure 7A:
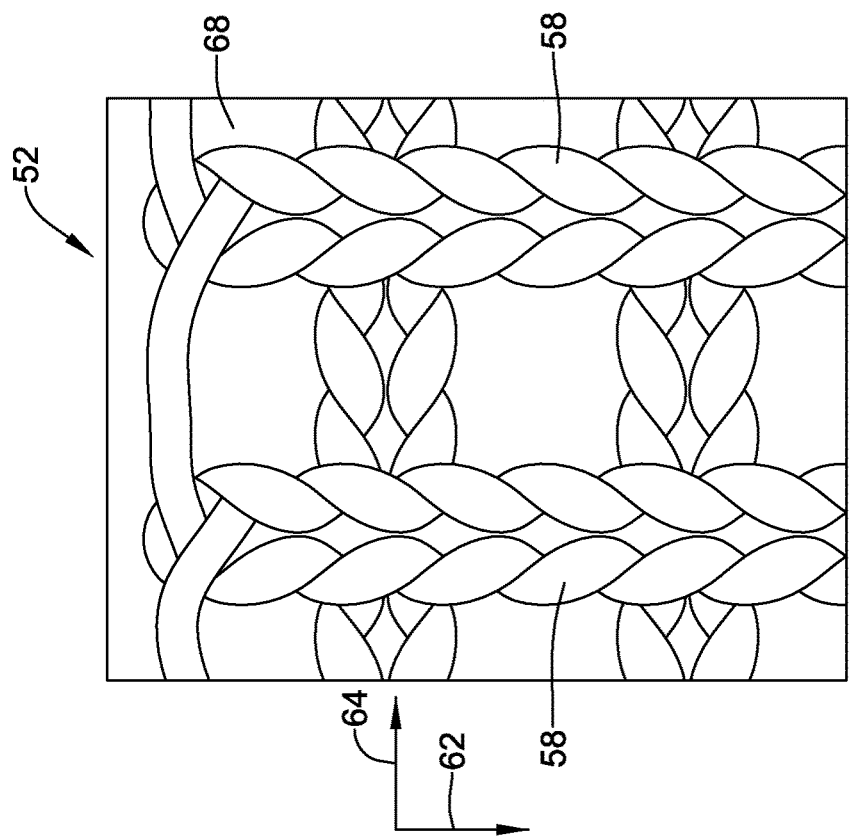
FIG. 7A is a top view of an illustrative layer of a spacer fabric.

In the illustrative spacer fabric 50 shown in FIG. 6, the top layer 52 may include a plurality of openings or spaces 68 positioned between the weft and the warp strand(s) 58 while the bottom layer 54 may be formed with a tighter knit such that any gaps between the weft and the warp strand(s) 58 are smaller than that of the top layer 52, which can be more clearly seen in FIGS. 7A and 7B which illustrate a top view of the top layer 52 and a bottom view of the bottom layer 54, respectively. A knit structure having gaps or openings 68 may have more flexibility, compliance, and/or stretchability compared to a tighter knit with fewer openings therein. While the illustrative spacer fabric 50 of FIG. 6 does not illustrate the exact knots, knit stitches and/or weave used to form the top layer 52 and/or bottom layer 54, it should be understood that the strands 58 do not necessarily extend in the weft direction 62 and/or warp direction 64 in a straight or linear manner (e.g., without knots or weaving).

The spacer filaments 56 may extend between the top layer 52 and the bottom layer 54 in a thickness direction 66. The spacer filaments 56 may be the same strand 58 (or strands) used to form the top layer 52 and/or bottom layer 54. For example, if a single strand is utilized to form the spacer fabric 50, said strand would form all of the spacer filaments 56 as well as the top layer 52 in the bottom layer 54. In some examples, the spacer filaments 56 may be formed from a different material than a bulk of the top layer 52 and/or bottom layer 54. In such an example, the spacer filaments 56 may be selectively interwoven or knitted into and between the top layer 52 and the bottom layer 54.

Once the spacer fabric 50 is complete, the spacer fabric 50 may be cut through the spacer filaments 56, for example, at line 70 to form two separate self-fixating meshes (e.g., one from top layer 52 and one from bottom layer 54) each having a plurality of micro-pillars (e.g., spacer filaments 56) extending therefrom. It is contemplated that the spacer fabric 50 may be annealed, cauterized, or otherwise processed (either before or after cutting) in order to reduce or eliminate unraveling of the strands 58. In some instances, the spacer filaments 56 may be mechanically cleaved using for example a blade, knife, scissors, etc. In other instances, the spacer filaments 56 may be cut through the use of heat. It is contemplated that the use of heat may create some melt back on the cut ends of the spacer filaments which may improve the ability of the ends of the spacer filaments 56 to grip. In some examples, the spacer filaments 56 may be further processed after cutting in order to further improve the self-fixating characteristics.

Figure 8:
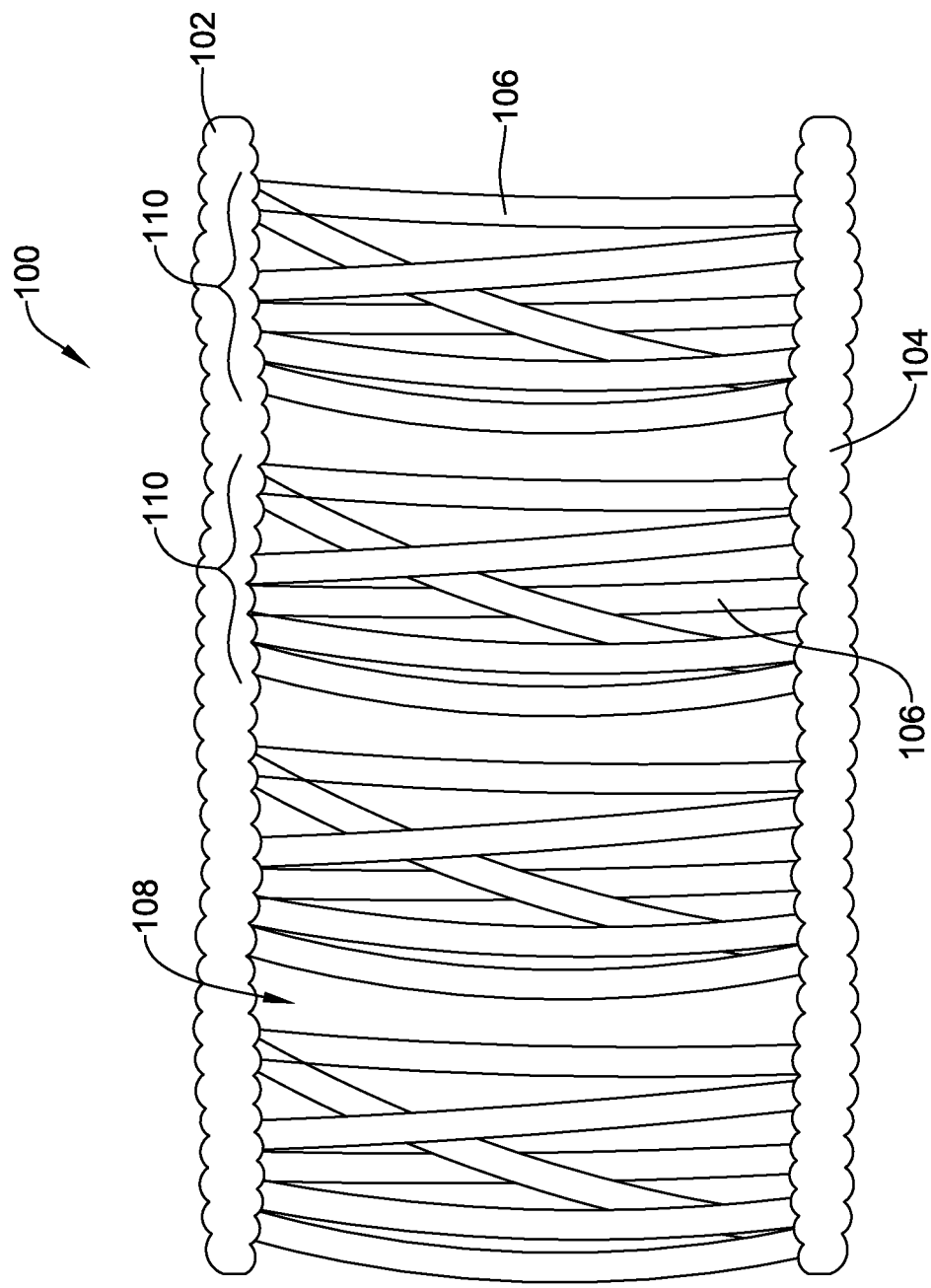
FIG. 8 is a side view of an illustrative spacer fabric.

As described herein, the spacer filaments 56 may extend between the top layer 52 and the bottom layer 54 at any angle between 0° and 180°. It is further contemplated that the spacer filaments 56 may be arranged in a pattern or eccentrically, as desired. FIG. 8 illustrates a side view of one illustrative spacer fabric 100. In FIG. 8, the spacer filaments 106 extend between a top layer 102 and a bottom layer 104 such that channels 108 are positioned between adjacent groups 110 of the spacer filaments 106. The spacer filaments 106 do not all necessarily have the same angle between top layer 102 and bottom layer 104. As can be seen in FIG. 8, some spacer filaments 106 extend at non-orthogonal angles while other spacer filaments 106 extend at a generally orthogonal angle.

Figure 9:
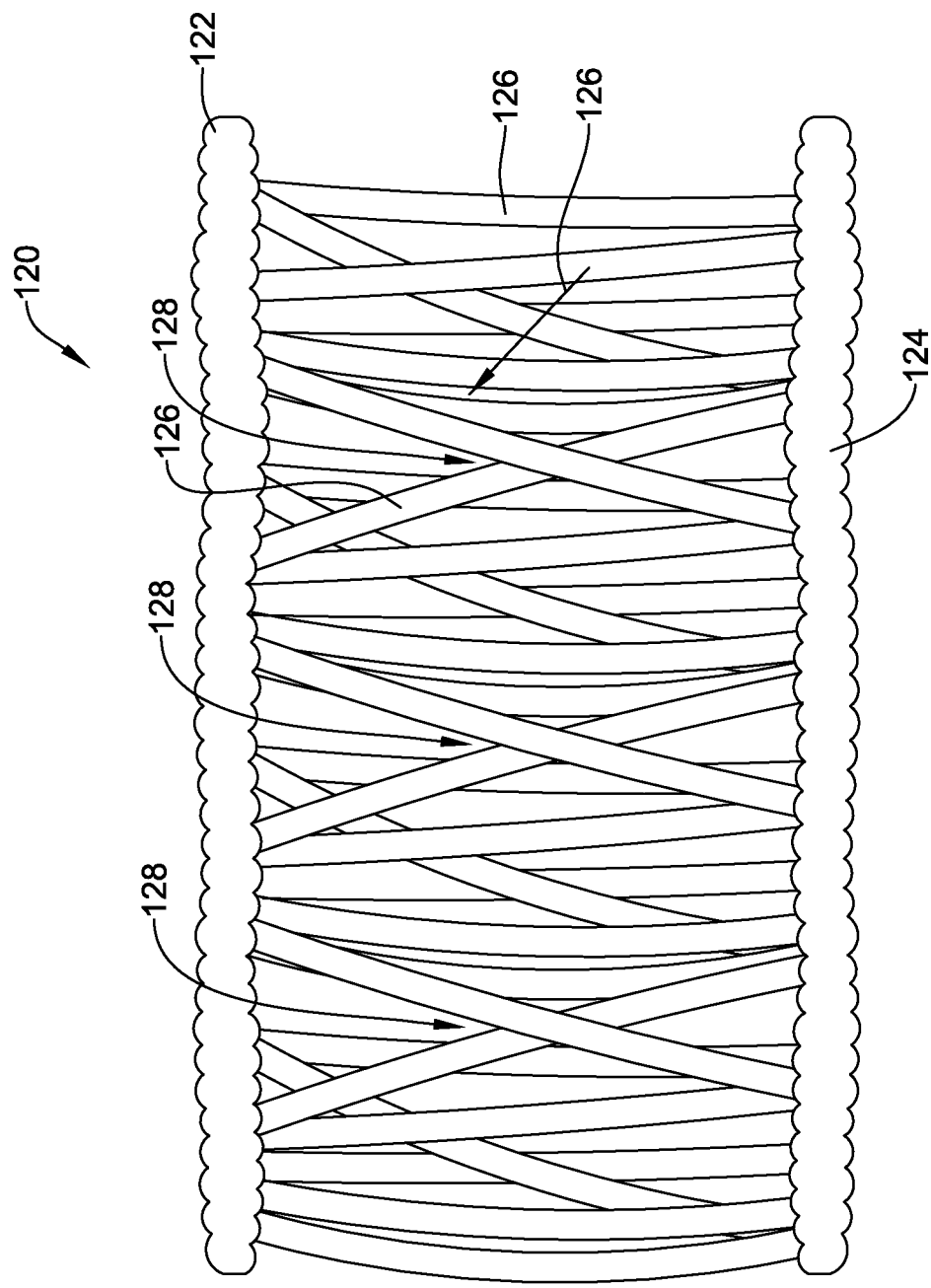
FIG. 9 is a side view of another illustrative spacer fabric.
Figure 10:
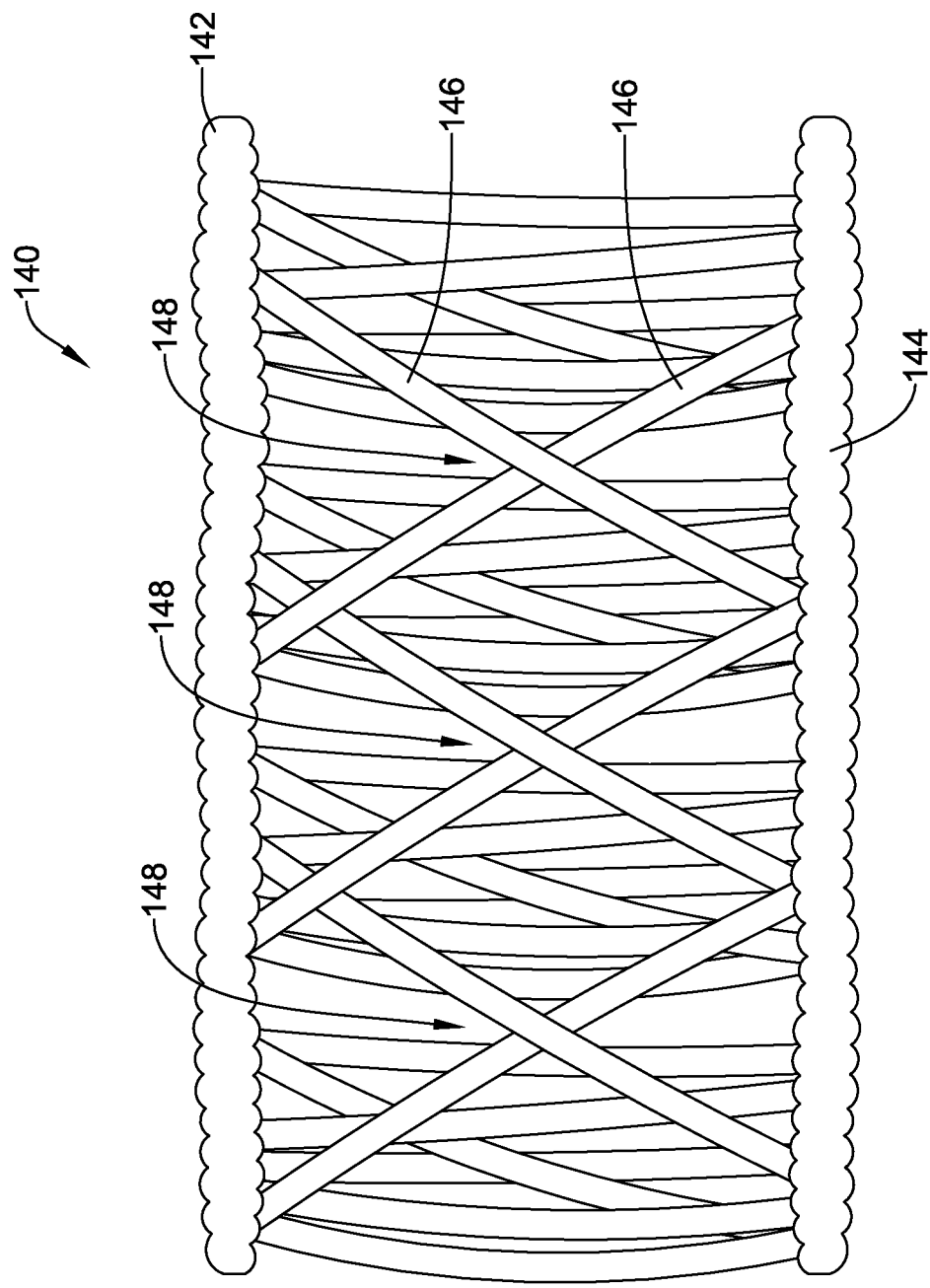
FIG. 10 is a side view of another illustrative spacer fabric.

FIG. 9 illustrates a side view of another illustrative spacer fabric 120. In FIG. 9, the spacer filaments 126 extend between a top layer 122 and a bottom layer 124 at generally non-orthogonal angles such that a plurality of cross points 128 are present. FIG. 10 illustrates a side view of another illustrative spacer fabric 140. In FIG. 10, the spacer filaments 146 extend between a top layer 142 and a bottom layer 144 at generally non-orthogonal angles (different from that of FIG. 9) such that a plurality of cross points 148 are present.

Figure 11:
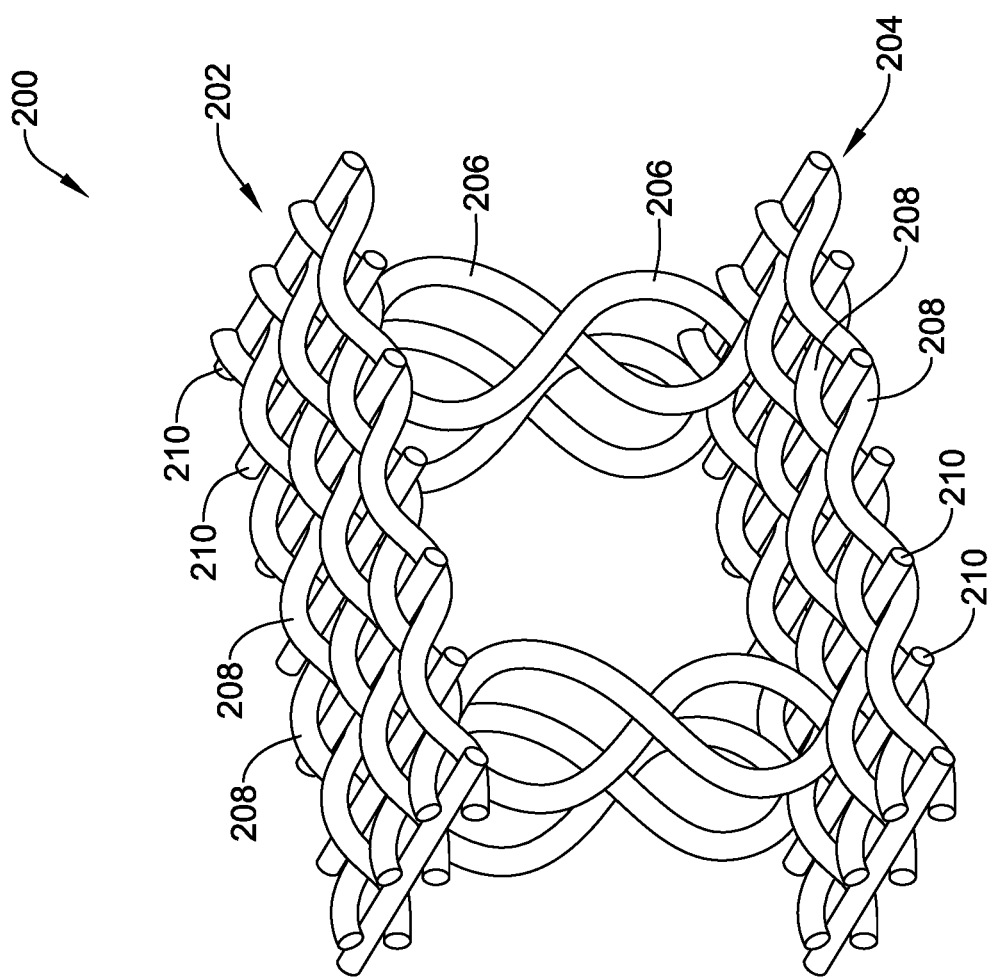
FIG. 11 is a perspective view of another illustrative spacer fabric for forming a self-fixating mesh.

FIG. 11 is a perspective view of a portion of another illustrative spacer fabric 200. The spacer fabric 200 may include a top layer 202, a bottom layer 204 and a plurality of spacer filaments 206. The top layer 202 and the bottom layer 204 may have a generally woven structure including one or more warp strands 208 and one or more weft strands 210. As described above, the strands 208, 210 may be monofilament, multifilament, or combinations thereof. Further, the strands 208, 210 may be formed of the same or different materials, as desired. As the layers 202, 204 are woven, intermittently (e.g., at uniform intervals or eccentrically, as desired) a strand 208 may extend from one layer to the other (e.g., from the top layer 202 to the bottom layer 204 or vice versa) to form the spacer filament 206 which are then interwoven into the opposing layer 202, 204. While the spacer filaments 206 are illustrated as having an undulating configuration, this is not required. It is contemplated that the spacer filaments 206 may extend generally orthogonally or at a non-orthogonal angle as described herein, as desired. A tightly woven spacer fabric 200 may exhibit minimal compliance or a reduced ability to stretch. The compliance or stretch ability may be manipulated by omitting one or more warp strands 208 and/or one or more weft strands 210 to create a looser weave in the top layer 202 and/or bottom layer 204. As described herein, once the spacer fabric 200 has been formed, the spacer fabric 200 may be split through the spacer filaments 206 to create a first self-fixating mesh from the top layer 202 and a second self-fixating mesh from the bottom layer 204 where the spacer filaments 206 form the micro-pillars.

Figure 12:
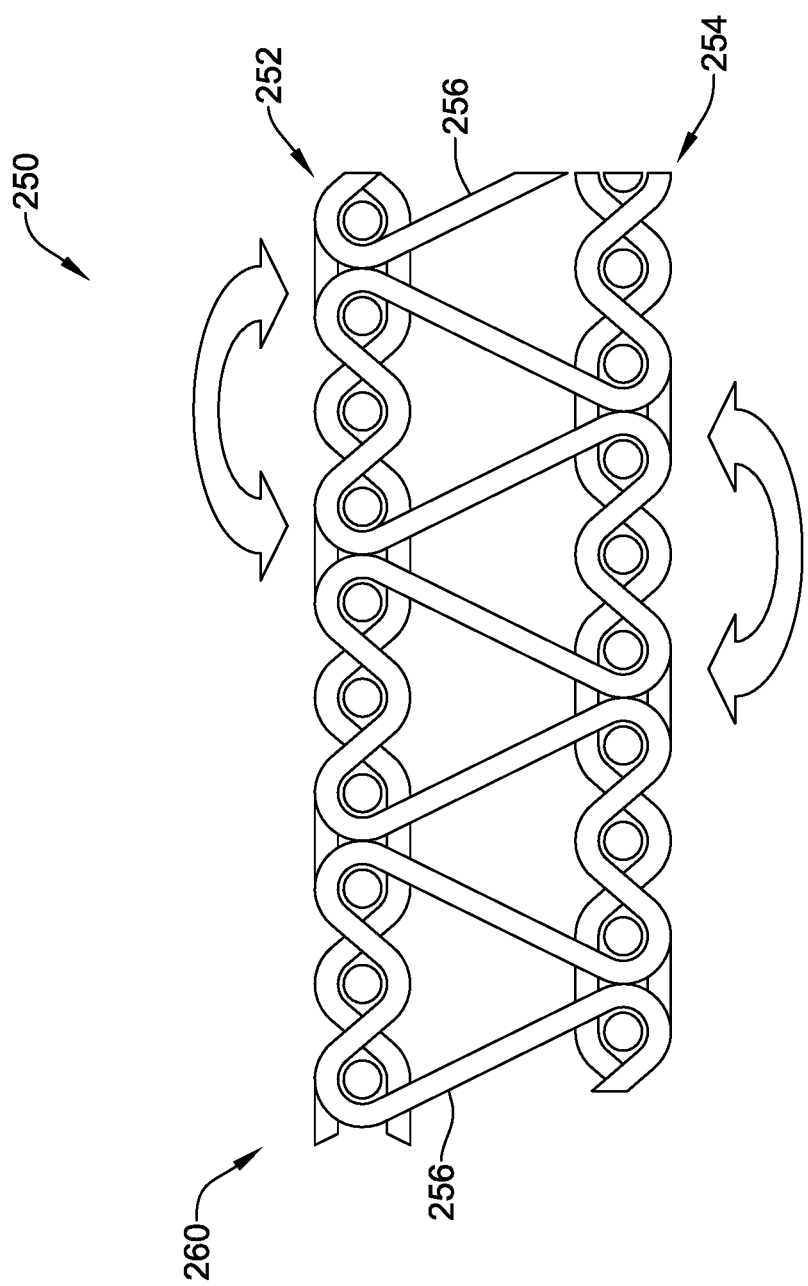
FIG. 12 is a partial cross-sectional view of another illustrative spacer fabric for forming a self-fixating mesh.

FIG. 12 is a partial side view of another illustrative spacer fabric 250 in which a velvet material 260 is utilized to form the self-fixating mesh. The velvet 260 may similarly be formed with a top layer 252 a bottom layer 254 a plurality of interconnecting filaments 256. The interconnecting filaments 256 may be interwoven in a predetermined pattern where the interconnecting filaments 256 extend at generally non-orthogonal angles to the top layer 252 and/or bottom layer 254. As described herein, once the spacer fabric 250 has been formed, the spacer fabric 250 may be split using through the spacer filaments 256 to create a first self-fixating mesh from the top layer 252 and a second self-fixating mesh from the bottom layer 254 where the spacer filaments 256 form the micro-pillars.

As described herein, it may be desirable to position the implant 10 and the self-fixating mesh 30 within a vessel to permanently or temporarily occlude the vessel. Referring now to FIGS. 13-16, a method for delivering and implanting the implant 10 within a vessel of the body will now be described. A delivery system 300 may be introduced into the vasculature through, for example, the femoral vein, or directly into the vessel to be treated. In some instances, the delivery system 300 may be introduced in combination with other devices, such as, but not limited to, an introducer sheath. These are just examples. It is contemplated that the delivery system 300 may be introduced through any location desired and with or without the use of an introducer sheath or other auxiliary component. The delivery system 300 may be advanced through the vasculature to the desired treatment location, which, in the case of venous reflux may be a vessel within the pelvic region or lower extremities. In some instances, the delivery system 300 may be advanced through the vasculature with the implant 10 preloaded within a lumen 320 thereof. Alternatively, in some cases, the delivery system 300 may be advanced to a desired treatment location and the implant 10 subsequently advanced within the lumen 320 of the delivery system 300.

Figure 13:
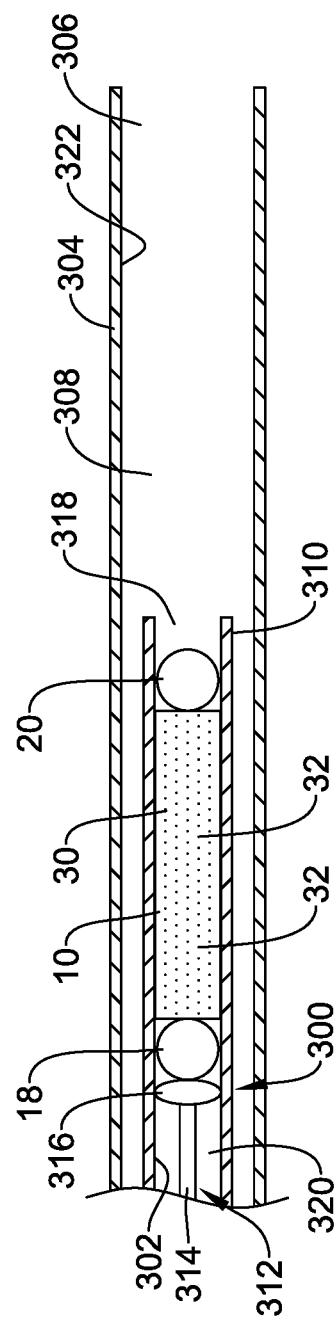
FIGS. 13-17 are schematic views illustrating the use of a delivery system to deploy an implant.

FIG. 13 is a partial cross-sectional view of the delivery system 300 disposed within the lumen 306 of a vessel 304 with the distal end 310 of the delivery system 300 adjacent to a target treatment region 308. In some instances, the delivery system 300 may include an elongate shaft 302, such as but not limited to a guide catheter, which may extend from a proximal end region configured to remain outside of the body to a distal end 310 configured to be positioned adjacent to the desired treatment region 308. In some examples, the proximal end region of the guide catheter 302 may be configured to couple to auxiliary treatment devices. The guide catheter 302 may further include a pusher element 312 slidably disposed within the lumen 320 thereof. The pusher element 312 may include having an elongate shaft 314 and a pusher head 316. The elongate shaft 314 of the pusher element 312 may extend proximally to a proximal end region configured to remain outside the body. In some instances, the proximal end region of the elongate shaft 314 may include a handle to facilitate manipulation of the pusher element 312, although this is not required. The pusher element 312 may be configured to exert a distal pushing force on the first end portion 18 of the implant 10 to distally advance the implant 10 through a distal opening 318 of the guide catheter 302.

Figure 14:
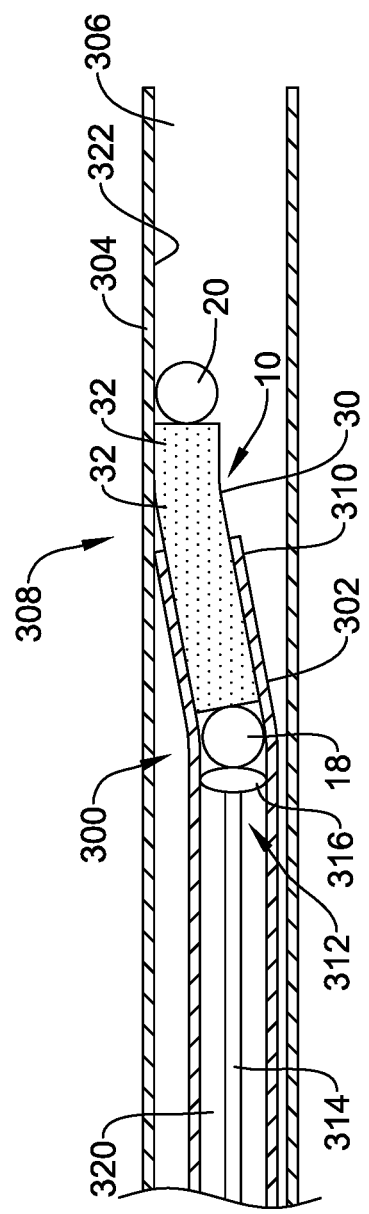

Referring additionally to FIG. 14, the distal end 310 of the guide catheter 302 may be configured to be deflectable, articulable, or steerable to deflect the distal opening 318 of the guide catheter 302 towards the wall 322 of the vessel 304. For example, the guide catheter 302 may include one or more articulation or deflection mechanism(s) that may allow for the guide catheter 302, or portions thereof, to be deflected, articulated, steered and/or controlled in a desired manner. For example, the guide catheter 302 may include at least a portion thereof that can be selectively bent and/or deflected in a desired or predetermined direction. This may, for example, allow a user to orient the guide catheter 302 such that the distal opening 318 is in a desirable position or orientation for navigation or delivery of the implant 10 to a target location. The guide catheter 302 may be deflected, for example, along a deflection region. A wide variety of deflection mechanisms may be used. In some example embodiments, deflection may be affected by one or more actuation members, such as pull wire(s) extending between a distal portion 310 of the guide catheter 302 and an actuation mechanism (not explicitly shown) near the proximal end region of the guide catheter 302.

In other embodiments, other articulation and/or deflection mechanism(s) are contemplated. For example, all or a portion of the guide catheter 302 may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the guide catheter 302 in a desired manner. Other suitable deflection mechanism(s) that are able to deflect the guide catheter 302 may also be used. Such alternative mechanisms may be applied to all other embodiments shown and/or discussed herein, and others, as appropriate.

Furthermore, the guide catheter 302 may include one or more predefined or fixed curved portion(s) along the length thereof. In some cases, such curved sections may be configured to fit with particular anatomies or be configured for better navigation or delivery of the implant 10. For example, a curved portion may be configured to direct the distal opening 318 of the guide catheter 302 towards the vessel wall 322. Additionally, or alternatively, some such curved sections may be configured to allow the guide catheter 302 to be predisposed to be bent and/or deflected in a certain direction or configuration when compression and/or tension forces are applied thereto. It is contemplated that the guide catheter 302 may be a laser cut metallic tubing, a braid reinforced polymeric tubing, or other flexible tubular structure as desired.

Once the distal opening 318 is directed towards the vessel wall 322, the pusher element 312 may be advanced distally to push the second end portion 20 of the implant 10 out of the distal end 310 of the guide catheter 302. As the implant 10 exits the guide catheter 302 towards the vessel wall 322 the micro-pillars 32 of the self-fixating mesh 30 may grip and/or attach to a side wall 322 of the vessel 304. As described herein, the intermediate rod portion 24 of the implant 10 may be bendable or flexible. This may allow the portion of the implant 10 immediately exiting the guide catheter 300 to be directed towards the vessel wall 304 while allowing the portion that has already exited the guide catheter 300 to remain fixated to the vessel wall 304, as shown in FIG. 14.

Figure 15:
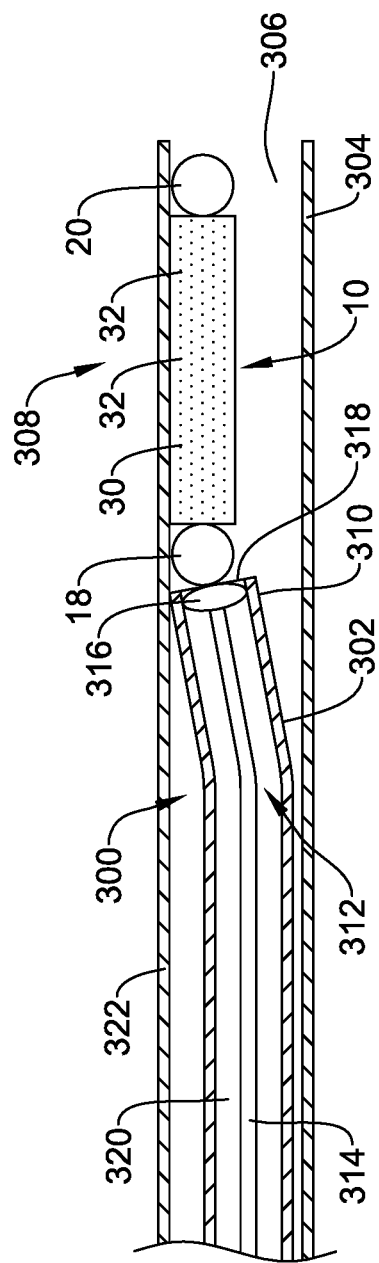
Figure 16:
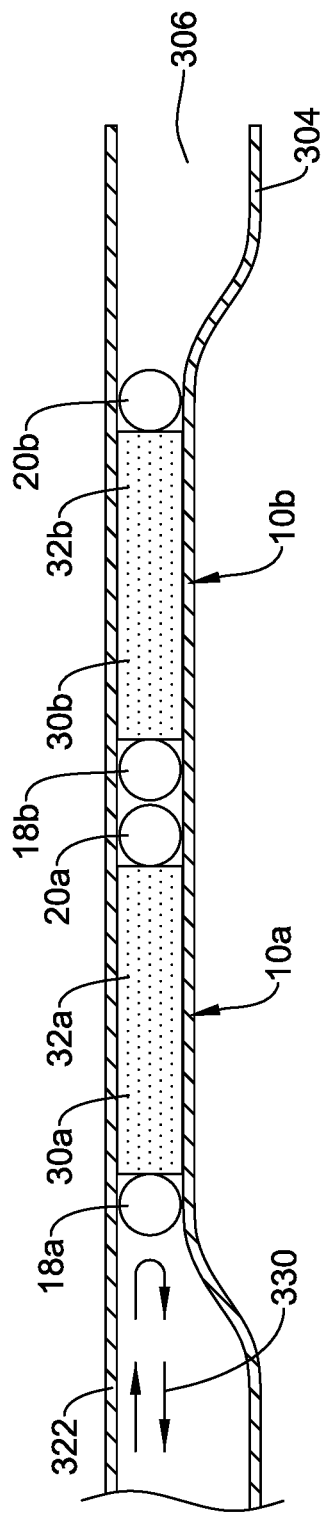

The pusher element 312 may be used to distally advance the implant 10 until an entire length thereof is advanced from the guide catheter 300, as shown in FIG. 15. It is contemplated that an entire length of the self-fixating mesh 30 may be fixated to the vessel wall 304 at a contact region between the vessel wall 322 and the mesh 30. It is contemplated that a plurality of implants 10 (e.g., two or more) may be positioned end to end within the lumen 306, as shown in FIG. 16, for example. The number of implants 10 desired may be selected to correspond to the length of the vessel to be occluded, a length of the implant 10, curvature of the vessel, or any combination thereof. In some cases, the desired number of implants 10 to be positioned within the vessel 304 may all be pre-loaded into the guide catheter 302. It is contemplated that a physician may remove any number of pre-loaded implants 10 to arrive at a chain of implants 10 having the desired length. In other cases, the implants 10 may be loaded and delivered one after another. For example, a first implant 10 may be delivered and positioned within the vessel 304, the pusher element 312 removed from the guide catheter 302, a second implant 10 advanced through the lumen 320 with the pusher element 312, delivered and positioned with the vessel 304. This procedure may be repeated until the desired number of implants 10 (e.g., spanning the desired length of the treatment region) has been delivered. The delivery system 300 and implants 10 may be supplied as a kit. In the kit, the implants 10 may be preloaded within a guide catheter 302 or separately provided, as desired.

Once delivery of the implant(s) 10 is complete, the delivery system 300 may be removed from the vasculature. The vessel 304 may then be made to contract about the outer surface of the implant(s) 10. FIG. 16 illustrates a first implant 10a and a second implant 10b (collectively, implants 10) positioned within the vessel 304 and having the vessel wall 322 collapsed thereon. While the vessel 304 is illustrated as having two implants 10, fewer than two or more than two implants may be provided within the vessel 304, as necessary to occlude the desired length of the vessel 304. The implants 10 may include each include a first end portion 18a, 18b (collectively, 18), a second end portion 20a, 20b (collectively, 20), and a self-fixating mesh 30a, 30b (collectively, 30) having a plurality of micro-pillars 32a, 32b (collectively, 32) extending radially therefrom. The vessel 304 may be made to contract about the outer surface of the implants 10 such that an inner surface of the vessel wall 322 is collapsed onto the outer surface of the implant 10. As the vessel wall 322 contacts the micro-pillars 32 on the outer surface of the self-fixating mesh 30, the micro-pillars 32 grip the vessel wall 322 and maintain the vessel 304 in a collapsed configuration. The generally solid structure of the implant 10 occludes the vessel lumen 306 preventing blood flow, as indicated at arrow 330. The blood can automatically reroute into other veins.

In one example, the vessel 304 may be collapsed by exerting a physical force (e.g., manual compressions) on a surface of a patient's body above the target region. For example, a clinician may use his or her hands to apply an external pressure to the vessel 304. Alternatively, or additionally, a pneumatic thigh cuff may be used to apply a pressure to the vessel 304. In some instances, this may require shifting a position of the patient and applying pressure while the patient is in a number of different positions as vessels may have a tendency to flatten (e.g., form an oval shape) when a patient is lying down.

Figure 17:
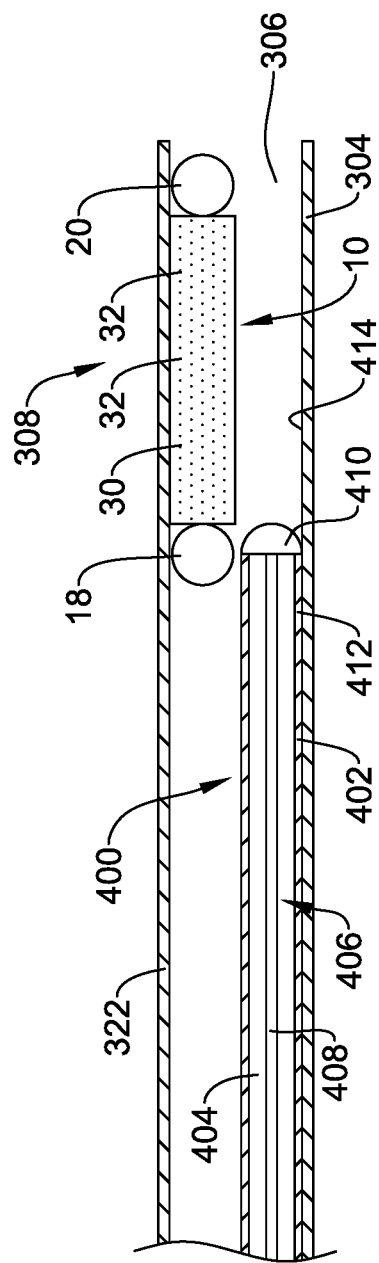

In another example, the vessel 304 may be collapsed using a negative pulse wave to induce a spasm in the vessel wall 322. Referring additionally to FIG. 17, after the implant 10, or plurality of implants, have been positioned against the vessel wall 322, the delivery system 300 may be removed. A stimulation catheter 400 may be advanced through the vasculature in place of the delivery system 300. The stimulation catheter 400 may include an elongate shaft 402 defining a lumen 404 therethrough. The stimulation catheter 400 may extend from a proximal end region configured to remain outside of the body to a distal end region 412 configured to be positioned adjacent to the implant 10. A stimulation probe 406 having an electrode 410 may be fixedly or slidably disposed within the lumen 404 of the elongate shaft 402. The electrode 410 may be disposed at or adjacent to the distal end region 412 of the elongate shaft 402. The electrode 410 may be in electrical communication with a battery (such as, but not limited to a 9-Volt battery) or other power source disposed within a handle (or other component) positioned outside the body by one or more electrical conductors 408. While not explicitly shown a ground pad may be placed on the skin of the patient to complete the electrical circuit.

The electrode 410 may be drug or slid along the vessel wall in the regions in which vessel constriction is desired. It is contemplated that the stimulation catheter 400 may be sized to fit in the vessel 304 between the implant 10 and the opposing side wall 414. As the stimulation catheter 400 is drug along the wall an intermittent negative pulse wave (e.g. in the range of 1 to 5 Volts for in the range of 1 to 100 milliseconds, which may reliably cause vasospasm in both arteries and veins) may be generated. This may initiate vasospasm in the vessel 304 which may cause the remainder of the vessel wall 322 (not already in contact with self-fixating mesh 30) to contact the self-fixating mesh 30 and adhere thereto thus collapsing the vessel 304 and occluding the vessel 304, as shown in FIG. 16. In some embodiments, the delivery system 300 may be configured to deliver an electrical impulse as the implant(s) 10 are delivered to induce localized vasospasm as each implant 10 is delivered. It is further contemplated that the delivery system 300 may use mechanical irritation of the vessel 304 to induce vasospasm. In one example, the guide catheter 302 may include one or more wires wrapping about a circumference of the catheter 302 and extending radially outward therefrom near the distal end region 310. The wires may scrape the vessel wall 322 as the guide catheter 302 is withdrawn from the vessel, causing vasospasm around the implants 10.

Alternatively, or additionally to, mechanical compressions, electrically induced vasospasms, and/or mechanically induced vasospasms, vasospasm inducing drugs may be used to induce vasospasm. For example, an outer surface of the implant 10 (e.g., portions or all of body portion 11 and/or mesh 30) may be coated with a vasospasm inducing drug to induce local vasospasm. Some illustrative vasospasm inducing drugs may include, but are not limited to, Endothelin 1, norepinephrine, U46619 (a stable synthetic analog of the endoperoxide prostaglandin PGH2), and/or Thromboxane A2 (TXA2). Additionally, or alternatively, the outer surface of the implant 10 (e.g., portions or all of body member 11 and/or mesh 30) may be coated with a sclerosant to help initiate vasospasm and endothelial damage, which may further help close the vessel 304.

It is contemplated that any of the methods described herein may be used individually or in combination with other methods. It is further contemplated that vasoconstriction may be executed in a stepped or incremental manner. For example, gradual vessel closure may allow the body to adapt and compensate accordingly. In one example, this may be achieved through incremental stepped mechanical compressions performed at a prescribed interval. In another example, stepped vasoconstriction may be achieved through the natural movement of the patient.

The materials that can be used for the various components of the implant 10, the delivery system 300, and/or the stimulation system 400, etc. (and/or other systems disclosed herein) and the various elements thereof disclosed herein may include those commonly associated with medical devices. For simplicity purposes, the following discussion makes reference to the implant 10, the delivery system 300, and/or the stimulation system 400, etc. However, this is not intended to limit the devices and methods described herein, as the discussion may be applied to other elements, members, components, or devices disclosed herein, such as, but not limited to, the implant 10, the delivery system 300, and/or the stimulation system 400, etc. and/or elements or components thereof.

In some embodiments the implant 10, the delivery system 300, and/or the stimulation system 400, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the implant 10, the delivery system 300, and/or the stimulation system 400, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the implant 10, the delivery system 300, and/or the stimulation system 400, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the implant 10, the delivery system 300, and/or the stimulation system 400, etc. to achieve the same result.

In some embodiments, a degree of Magnetic Resonance Imaging (MRI) compatibility is imparted into the implant 10, the delivery system 300, and/or the stimulation system 400, etc. For example, the implant 10, the delivery system 300, and/or the stimulation system 400, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The implant 10, the delivery system 300, and/or the stimulation system 400, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the implant 10, the delivery system 300, and/or the stimulation system 400, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the implant 10, the delivery system 300, and/or the stimulation system 400, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the implant 10, the delivery system 300, and/or the stimulation system 400, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments the implant 10, the delivery system 300, and/or the stimulation system 400, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/ antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms. Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An implant for occluding a flow through a vessel, the implant comprising:
   a body member having a first end portion, a second end portion, and an intermediate rod portion extending between the first end portion and the second end portion, the intermediate rod portion having an outer diameter less than an outer diameter of the first end portion and an outer diameter of the second end portion; and
   a mesh having a base layer and a plurality of micro-pillars extending from a first surface of the base layer, the mesh disposed about the intermediate rod portion such that an inner diameter of the mesh is less than the outer diameter of the first end portion and the outer diameter of the second end portion and such that the micro-pillars extend generally radially outward from the body member;
   wherein the plurality of micro-pillars are configured to extend into an adjacent tissue; and
   wherein the body member has a generally solid structure.

2. The implant of claim 1, wherein the mesh is disposed about the intermediate rod portion.

3. The implant of claim 1, wherein the intermediate rod portion is configured to bend.

4. The implant of claim 1, wherein the first end portion and the second portion have a generally spherical shape.

5. The implant of claim 1, wherein the implant has a generally uniform outer diameter.

6. The implant of claim 1, wherein the base layer is a knitted fabric formed from one or more strands.

7. The implant of claim 6, wherein the micro-pillars are knitted into the base layer.

8. The implant of claim 1, wherein the base layer is a woven fabric formed from one or more strands.

9. The implant of claim 8, wherein the micro-pillars are woven into the base layer.

10. The implant of claim 1, wherein the mesh is disposed over the intermediate rod portion and at least a portion of one or both the first or second end portions.

11. A method for delivering an implant to a body vessel, the method comprising:
    advancing a guide catheter and an implant within a body vessel, the implant comprising:
       a body member having a first end portion, a second end portion, and an intermediate rod portion extending between the first end portion and the second end portion; and a mesh having base layer and a plurality of micro-pillars extending from a first surface of the base layer, the mesh disposed about at least a portion of the body member such that the micro-pillars extend generally radially outward from the body member;

positioning a distal end region of the guide catheter adjacent to a target region within the body vessel;

directing a distal opening of the guide catheter towards a side wall of the body vessel;

distally advancing the implant through the distal opening of the guide catheter towards the side wall of the body vessel; and compressing an inner surface of the vessel about an outer surface of the implant;

wherein as the implant is distally advanced through the distal opening of the guide catheter, the plurality of micro-pillars along a portion of the mesh are pushed into the side wall of the vessel.

12. The method of claim 11, wherein compressing the inner surface of the vessel about an outer surface of the implant comprises exerting a physical force on a surface of a patient's body above the target location.

13. The method of claim 12, wherein the physical force is a pneumatic cuff.

14. The method of claim 11, wherein compressing the inner surface of the vessel about an outer surface of the implant comprises delivering a negative pulse wave to the vessel adjacent to the target region.

15. The method of claim 14, wherein delivering the negative pulse wave comprises advancing a stimulation catheter having an electrode through the body vessel to the target region.

16. The method of claim 11, wherein compressing the inner surface of the vessel about an outer surface of the implant comprises delivering a vasospasm inducing drug to the target region.

17. The method of claim 16, wherein the vasospasm inducing drug is coated on an outer surface of the implant.

18. An implant and delivery system kit, the kit comprising:

one or more implants, the one or more implants comprising:
　a generally solid body member having a first end portion, a second end portion, and an intermediate rod portion extending between the first end portion and the second end portion, the intermediate rod portion having an outer diameter less than an outer diameter of the first end portion and an outer diameter of the second end portion; and
　a mesh having base layer and a plurality of micro-pillars extending from a first surface of the base layer, the mesh disposed about the intermediate rod portion such that the micro-pillars extend generally radially outward from the body member; and a delivery system, the delivery system comprising:
　a guide catheter defining a lumen extending from a proximal end region to a distal opening; and
　a pusher element having an elongate shaft and pusher head positioned at a distal end of the elongate shaft.

19. The kit of claim 18, wherein the one or more implants are pre-loaded within the lumen of the guide catheter.

* * * * *